(12) United States Patent
Chavan et al.

(10) Patent No.: US 11,432,845 B2
(45) Date of Patent: Sep. 6, 2022

(54) INSERTION TOOL WITH A DISSECTOR

(71) Applicant: Senseonics, Incorporated, Germantown, MD (US)

(72) Inventors: Abhi Chavan, Germantown, MD (US); Bryan Hays, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 133 days.

(21) Appl. No.: 16/844,043

(22) Filed: Apr. 9, 2020

(65) Prior Publication Data

US 2020/0323557 A1 Oct. 15, 2020

Related U.S. Application Data

(60) Provisional application No. 62/831,286, filed on Apr. 9, 2019.

(51) Int. Cl.
*A61B 17/34* (2006.01)
*A61B 17/32* (2006.01)
*A61B 17/00* (2006.01)

(52) U.S. Cl.
CPC .... *A61B 17/3423* (2013.01); *A61B 17/00234* (2013.01); *A61B 17/32* (2013.01); *A61B 17/3496* (2013.01); *A61B 2017/00367* (2013.01); *A61B 2017/320044* (2013.01); *A61B 2017/320056* (2013.01); *A61B 2017/3456* (2013.01)

(58) Field of Classification Search
CPC .......... A61B 17/3423; A61B 17/00234; A61B 17/3496; A61B 17/3468; A61B 2017/00367; A61B 2017/320044; A61B 2017/320056; A61B 2017/3456; A61B 5/14532; A61B 5/14865; A61B 17/3415; A61B 17/3417; A61B 17/3421; A61B 17/34; A61B 17/3209
See application file for complete search history.

(56) References Cited

U.S. PATENT DOCUMENTS

| | | | |
|---|---|---|---|
| 7,655,014 B2 | 2/2010 | Ko et al. | |
| 7,867,199 B2 | 1/2011 | Mogensen et al. | |
| 7,927,331 B2 | 4/2011 | Gade | |
| 10,828,054 B2 | 11/2020 | Hays et al. | |
| 2014/0257272 A1 | 9/2014 | Clark, III et al. | |
| 2014/0324067 A1 | 10/2014 | Emken et al. | |
| 2015/0257787 A1 | 9/2015 | Haigh et al. | |
| 2018/0280056 A1 | 10/2018 | Austin et al. | |
| 2019/0192179 A1 | 6/2019 | Hays et al. | |
| 2020/0323557 A1 | 10/2020 | Chavan et al. | |

*Primary Examiner* — Brooke Nicole Labranche
(74) *Attorney, Agent, or Firm* — Rothwell, Figg, Ernst & Manbeck, P.C.

(57) ABSTRACT

An insertion tool for creating a subcutaneous pocket and implanting a device in the pocket. The tool may include a cannula extending from a handle, a dissector tip disposed at a distal end of the cannula, and a rod. The cannula and dissector tip may create the pocket. The cannula may include a passage and an opening into the passage, and the cannula may be disposed in the passage and move along the passage between a retracted position and an extended position. The rod and the cannula may be configured such that, when the rod is at the retracted position, the cannula holds the device in the passage, and as the cannula moves from the extended position to the retracted position, the rod forces the device through the opening at the distal end of the cannula, at least partially out of the cannula, and at least partially into the pocket.

7 Claims, 12 Drawing Sheets

INSERTION TOOL WITH A DISSECTOR

CROSS-REFERENCE TO RELATED APPLICATION

The present application claims the benefit of priority to U.S. Provisional Application Ser. No. 62/831,286, filed on Apr. 9, 2019, which is incorporated herein by reference in its entirety.

BACKGROUND

Field of Invention

This disclosure relates to a tunneling tool for creating a subcutaneous pocket below a skin surface and implanting a device in the subcutaneous pocket.

Discussion of the Background

Implantable devices may be implanted within a living animal (e.g., a human). Some implantable devices are implanted in subcutaneous tissue below the skin. Some implantable devices may detect the presence or amount of an analyte (e.g., glucose or oxygen) in a medium (e.g., blood or interstitial fluid) within the living animal.

Known tools for inserting an implantable device in subcutaneous tissue include a tunneling tool and an insertion tool. The tunneling tool may be used to create a tunnel and a subcutaneous pocket below a skin surface, and the insertion tool may be used to deliver the device through the tunnel and into the subcutaneous pocket.

However, when using the insertion tool, the device is typically exposed at the distal end of the insertion tool, such that the device leads the insertion tool through the tunnel below the skin surface. Often, the user has to rotate the insertion tool back and forth to force the device through the tunnel and position the device into the pocket. Such exposure and force may dislocate the device from the insertion tool before the device reaches the subcutaneous pocket and/or damage the device. Moreover, exposing the device at the distal end of the insertion tool while implanting the device may cause trauma to the inside of the pocket, which may result in more bleeding and may cause distortion in the signal transmitted from the device.

Accordingly, there is a need for an improved insertion tool to shield the device from exposure to the skin tissue during insertion and reduced trauma to the subcutaneous pocket while implanting the device. The improved insertion tool may thereby extend the longevity of the device and/or improve accuracy.

SUMMARY

Aspects of the present invention may relate to an improved insertion tool that shields an implantable device from exposure to the skin tissue during insertion. Embodiments of the improved insertion tool may reduce trauma to the subcutaneous pocket while implanting the device.

One aspect of the invention may provide an insertion tool creating a subcutaneous pocket below a skin surface and implanting a device in the subcutaneous pocket. In some embodiments, the insertion tool may include a handle. In some embodiments, the insertion tool may include a cannula extending from the handle, wherein the cannula comprises a passage and an opening into the passage at a distal end of the cannula. In some embodiments, the cannula may be configured to move in an axial direction between an extended position and a retracted position. In some embodiments, the insertion tool may include a dissector tip disposed at the distal end of the cannula, wherein the cannula and the dissector tip are configured to create the subcutaneous pocket below the skin surface. In some embodiments, the insertion tool may include a rod disposed in the passage of the cannula and configured to remain stationary relative to the handle in the passage of the cannula as the cannula moves between the extended and retracted positions. In some embodiments, the insertion tool may include an actuator disposed in the handle and operatively connected to the cannula such that the actuator is configured to move the cannula between the retracted and extended positions. In some embodiments, the rod and the cannula may be configured such that, when the cannula is at the extended position, the rod is spatially separated from the distal end of the cannula such that the cannula holds the device in the passage of the cannula. In some embodiments, the rod and cannula may be configured such that, when the cannula is at or about the retracted position, the rod is disposed proximate to the distal end of the cannula such that, as the cannula moves from the extended position to the retracted position, the rod forces the device through the opening at the distal end of the cannula, at least partially out of the cannula, and at least partially into the subcutaneous pocket.

In some embodiments, the dissector tip may comprise a sleeve around at least a portion of the cannula. In some embodiments, the sleeve may be configured to be pulled along the cannula from a closed position to an open position; wherein, in the closed position, the sleeve encloses the opening at the distal end of the cannula; and wherein, in the open position, the sleeve exposes the opening of the distal end of the cannula. In some embodiments, the sleeve may comprise one or more perforations configured to separate when the sleeve is pulled along the cannula from the closed position to the open position.

In some embodiments, the actuator may be operatively connected to the sleeve such that the actuator is configured to move the sleeve between the closed and open positions. In some embodiments, the actuator may be configured to move the sleeve from the closed position to the open position before moving the cannula from the extended position to the retracted position. In some embodiments, the actuator may be operatively connected to the sleeve such that the actuator is configured to move the sleeve between the closed and open positions. In some embodiments, the actuator may be to move the sleeve from the closed position to the open position before moving the cannula from the extended position to the retracted position.

In some embodiments, the distal end of the cannula may be bevel-shaped, and the dissector tip comprises a protrusion from the distal end of the cannula. In some embodiments, the insertion tool may comprise a sleeve around at least a portion of the cannula and enclosing the opening at the distal end of the cannula. In some embodiments, the sleeve may be configured to be pulled along the cannula from a closed position to an open position; wherein, in the closed position, the sleeve encloses the opening at the distal end of the cannula; and wherein, in the open position, the sleeve exposes the opening at the distal end of the cannula. In some embodiments, the sleeve may comprise one or more perforations configured to separate when the sleeve is pulled along the cannula from the closed position to the open position.

In some embodiments, the dissector tip may be blunt-shaped. In some embodiments, the distal end of the cannula may be bevel-shaped, and the dissector tip may comprise a flap coupled to the cannula, wherein the flap is configured to cover the opening at the distal end of the cannula. In some embodiments, the flap may be configured to pivot between a closed position, in which the flap encloses the opening of the distal end of the cannula, and an open position, in which the flap is spatially separated from the distal end of the cannula and exposes the opening at the distal end of the cannula. In some embodiments, the actuator may comprise a track extending along a portion of the handle and a slider knob configured to slide along the track and cause the rod to move between the retracted and extended positions.

One aspect of the invention may provide an insertion tool creating a subcutaneous pocket below a skin surface and implanting a device in the subcutaneous pocket. In some embodiments, the insertion tool may include a handle defining a cavity therein. In some embodiments, the insertion tool may comprise a tunneling tube extending from a first end of the handle and defining a passage opening into the cavity of the handle, and the tunneling tube is configured to move in an axial direction between an extended position and a retracted position. In some embodiments, the dissector may comprise a blunt tip configured to move between a retracted position, wherein the blunt tip is disposed in the cavity of the handle, and an extended position, wherein the blunt tip protrudes out of a distal end of the tunneling tube, and the dissector is configured to create the subcutaneous pocket. In some embodiments, the insertion tool may comprise an insertor comprising a cannula configured to move between a retracted position, wherein the cannula is disposed in the cavity of the handle, and an extended position, wherein the cannula is at least partially disposed in the passage of the tunneling tube. In some embodiments, the insertion tool may comprise an actuator disposed in the handle and operatively linked to the cannula, the dissector, and the insertor such that the actuator is configured to trigger the cannula, the blunt tip, and the cannula to move between the retracted and extended positions. In some embodiments, the tunneling tube and the cannula may be configured such that, when the tunneling tube and the cannula are at the extended position, the cannula holds the device in the passage of the cannula. In some embodiments, the tunneling tube and the cannula may be configured such that, when the tunneling tube is at or about the retracted position, the cannula moves toward the retracted position and releases the device out of the tunneling tube to deploy the device in the subcutaneous pocket.

In some embodiments, the dissector may be configured to pivot from an operating position disposed along a first axis defined by the tunneling tube to an idle position disposed along a second axis, and the inserter is configured to pivot from an idle position disposed disposed along a third axis to an operating position disposed along the first axis, wherein the second axis extends at a first acute angle with respect to the first axis, and third axis extends at a second acute angle with respect to the first axis. In some embodiments, the handle may comprise a hinge pivotably coupled to the dissector and the inserter. In some embodiments, the inserter may be configured to pivot between the operating and idle positions when the cannula tube is set in the retracted position, and the cannula tube is configured to move between the retracted and extended positions when the inserter is set at the operating position.

In some embodiments, the actuator may comprise a track extending along a portion of the handle and a slider knob configured to slide along the track and cause the tunneling tube, the blunt tip, and the cannula to move between the retracted and extended positions. In some embodiments, the dissector may comprise a first rod configured to move along the cavity of the handle and the passage of the tunneling tube, and the blunt tip is coupled to the first rod such that the first rod is configured to move the blunt tip along the cavity of the handle and the passage of the tunneling tube between the retracted and extended positions. In some embodiments, the insertor may comprise a second rod configured to move along the cavity of the handle and the passage of the tunneling tube, and the cannula comprises a first end configured to hold and release the device and a second end coupled to the second rod such that the second rod is configured to move the cannula along the cavity of the handle and the passage of the tunneling tube between the retracted and extended positions.

One aspect of the invention may provide a method of using an insertion tool to create a subcutaneous pocket below a skin surface and implant a device in the subcutaneous pocket. In some embodiments, the method may comprise a step of inserting a cannula of the insertion tool and a dissector tip disposed at a distal end of the cannula into an incision in the skin surface such that the dissector tip and the cannula create the subcutaneous pocket. In some embodiments, the method may comprise a step of moving the cannula in an axial direction from an extended position to a retracted position such that a rod disposed along a passage of the cannula forces the device through an opening at the distal end of the cannula, at least partially out of the passage of the cannula, and at least partially into the subcutaneous pocket.

In some embodiments, the method may further comprise loading the device into the passage of the cannula. In some embodiments, the method may further comprise after loading the device into the passage and before inserting the cannula and the dissector tip, pulling a sleeve around the distal end of the cannula to enclose the opening in the distal end of the cannula. In some embodiments, the method may further comprise before the step of loading, pulling a sleeve received around the cannula toward the handle to expose the opening in the distal end of the cannula. In some embodiments, the method may further comprise pulling the cannula away from the subcutaneous pocket.

In some embodiments, the method may further comprise using an actuator disposed in the handle to move the cannula from the extended position to the retracted position. In some embodiments, the method may further comprise pulling a sleeve along the cannula from a closed position, in which the sleeve encloses the opening at the distal end of the cannula, to an open position, in which the sleeve exposes the opening at the distal end of the cannula. In some embodiments, the method may further comprise a flap covers the opening at the distal end of the cannula, and moving the rod along the passage of the cannula from the retracted position to the extended position spatially separates the flap from the distal end of the cannula and exposes the opening at the distal end of the cannula.

Further variations encompassed within the insertion tools and methods are described in the detailed description of the invention below.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

DETAILED DESCRIPTION

Figure 1:
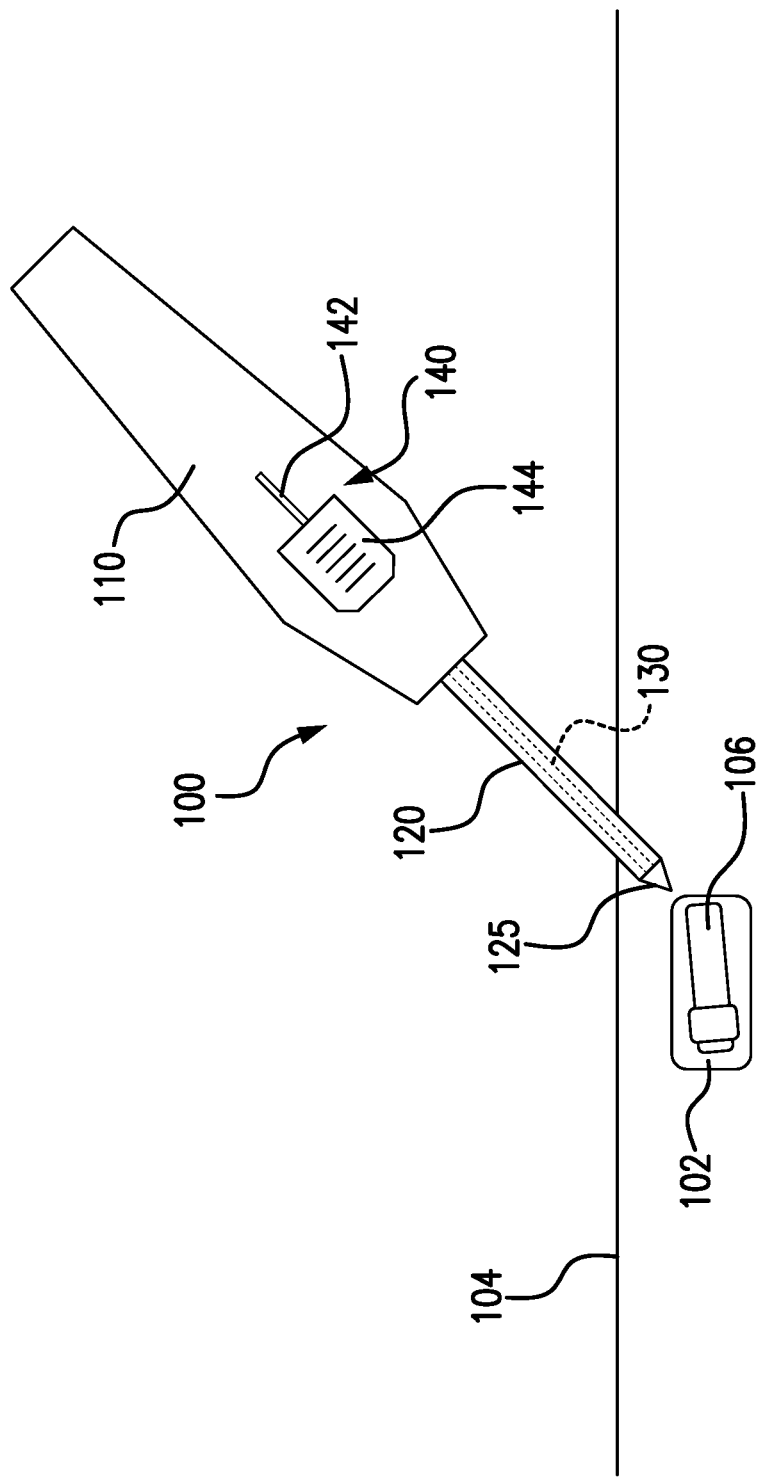
FIG. 1 is a schematic view of an insertion tool embodying aspects of the present disclosure.

FIG. 1 is a schematic view illustrating an exemplary insertion tool 100 embodying aspects of the present disclosure. In some embodiments, the insertion tool 100 may be for creating a subcutaneous pocket 102 below a skin surface 104 and implanting a device 106 in the subcutaneous pocket 102. In some non-limiting embodiments, the device 106 may include an RFID chip. In some non-limiting embodiments, the device 106 may include a sensor, such as, for example and without limitation, an analyte sensor (e.g., glucose sensor) and/or a temperature sensor. In some embodiments, the insertion tool 100 may include one or more of a handle 110, a cannula 120, a dissector tip 125, a rod 130, and an actuator 140.

In some embodiments, the cannula 120 may extend from the handle 110. In some embodiments, the cannula 120 may define a passage (e.g., through which the device 106 may pass). In some embodiments, the cannula 120 and dissector tip 125 may be configured to create the subcutaneous pocket below 102 the skin surface 104 by inserting the dissector tip 125 and cannula 120 into an incision (not shown) made in the skin surface 104. In some embodiments, the cannula 120 may be configured to move in an axial direction between an extended position and a retracted position. In some embodiments, when the cannula 120 is set at the extended position, the cannula 120 and the dissector tip 125 may be configured to create the subcutaneous pocket 102 below the skin surface 104. In some embodiments, movement of the cannula 120 to the retracted position may deploy the device 106 from within the passage of the cannula 120 into the subcutaneous pocket 102. In some embodiments, when the cannula 120 is set at the extended position, a substantial portion of the cannula 120 may be disposed outside the handle 110. In some embodiments, when the cannula 120 is set at the retracted position, a portion or all of the cannula 120 may be disposed in a cavity (not shown) of the handle 110.

In some embodiments, the rod 130 may be disposed (at least partially) in the passage of the cannula 120. In some embodiments, movement of the cannula 120 between the extended and retracted positions may be relative to the rod 130, which the rod 130 may be configured to remain stationary relative to the handle 110 in the passage of the cannula 120 as the cannula 120 moves between the extended and retracted positions. In some embodiments, when the cannula 120 is set in the extended position, the rod 130 may be spatially separated from a distal end of the cannula 120 so that the passage of the cannula 120 holds the device 106. In some embodiments, when the cannula 120 is moved from the extended position to the retracted position, the distal end of the cannula 120 may move toward the distal end of the rod 130, which may cause the rod 130 to act as a backstop and force the device 106 within the passage of the cannula 120 through an opening at the distal end of the cannula 120, at least partially out of the cannula 120, and at least partially into the subcutaneous pocket 120. In some embodiments, while or after retracting the cannula 120, a user may pull the handle 110 away from the pocket, leaving the device 106 in the subcutaneous pocket 120.

In some embodiments, the actuator 140 may be disposed in the handle 110 and may be operatively connected to the cannula 120. In some embodiments, the actuator 140 may be configured to move the cannula 120 between the retracted and extended positions. In some embodiments, the actuator 140 may include a track 142 extending along the handle 110 and a slider knob 144 configured to slide along the track 142. In some embodiments, movement of the slider knob 144 of the actuator 140 may force the cannula 120 to move between the extended and retracted positions. In some embodiments, the cannula 120 may be configured to move from the extended position to the retracted position by sliding the slider knob 144 along the track 142 in a direction away from the cannula 120. In some embodiments, the cannula 120 may be configured to move from the retracted position to the extended position by sliding the slider knob 144 along the track 142 in a direction toward the cannula 120. In other embodiments (not shown), the actuator 140 may additionally or alternatively include other mechanisms, such as, for example, a spring, a solenoid, or a motor, to bring about movement of the cannula 120.

FIGS. 2A-7C illustrate various exemplary embodiments of the cannula 120 and the inserter 130 that may be implemented with the insertion tool 100 according to the present disclosure.

Figure 2A:
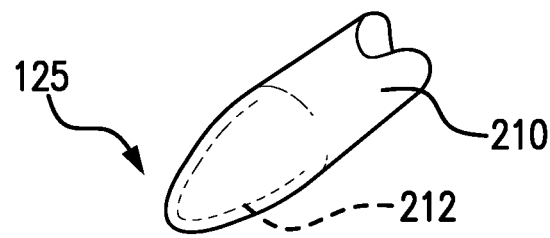
FIG. 2A is a perspective view of a dissector pull sleeve actuated tip in a closed position with the push rod retracted embodying aspects of the present disclosure.
Figure 2B:
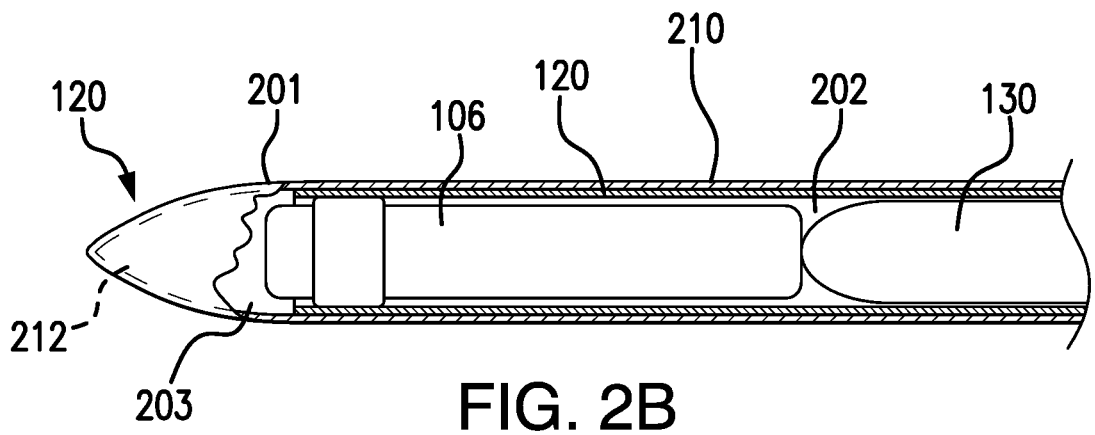
FIG. 2B is a cross-sectional side view of the pull sleeve actuated tip in the closed position with the push rod retracted embodying aspects of the present disclosure.
Figure 2C:
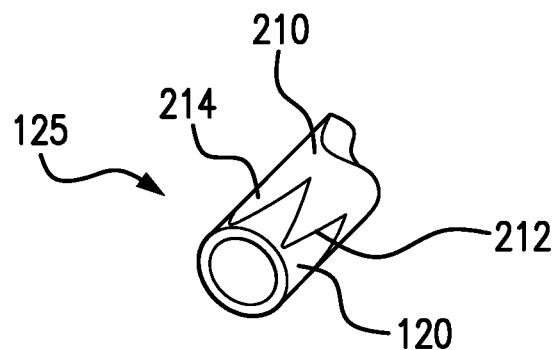
FIG. 2C is a perspective view of the dissector pull sleeve actuated tip in an open position with the push rod retracted embodying aspects of the present disclosure.
Figure 2D:
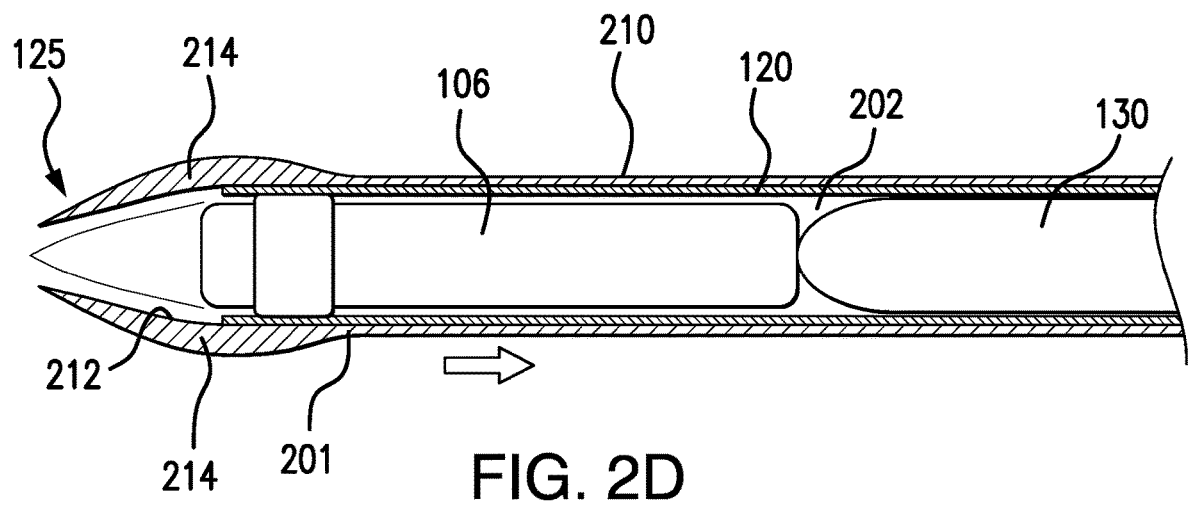
FIG. 2D is a cross-sectional side view of the dissector pull sleeve actuated tip in the open position with the push rod retracted embodying aspects of the present disclosure.

In some embodiments, as shown in FIGS. 2B and 2D, the cannula 120 may have a tubular shape and may define a passage 202 extending along a longitudinal axis of the cannula 120. In some embodiments, the cannula 120 may comprise a distal end 201 defining an opening 203 into the passage 202. In some embodiments, the distal end 201 of the cannula 120 may move in an axial direction away from the handle 110 when the cannula 120 is moving toward the extended position. In some embodiments, the distal end 201 of the cannula 120 may move in an axial direction toward the handle 110 when the cannula 120 is moving toward the retracted position. In some non-limiting embodiments, the cannula 120 may be comprised of, for example and without limitation, stainless steel. In some other non-limiting embodiments, the cannula 120 may be comprised of a polymeric material, such as, for example and without limitation, PC (polycarbonate), PPSU (polymer polyphenyl sulfone), PEEK (polyether ether ketone), PES (Polyethersulfone), POLY (polyacrylamide) . . . .

Figure 2E:
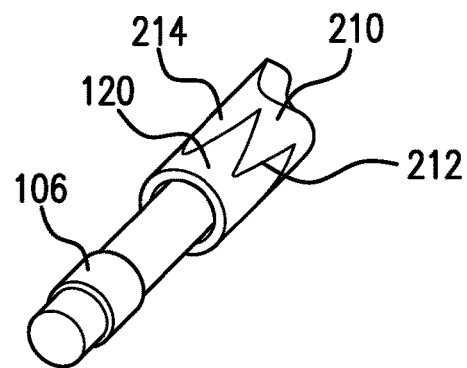
FIG. 2E is a perspective view of the dissector pull sleeve actuated tip in an open position with the push extended embodying aspects of the present disclosure.

In some embodiments, as shown in FIGS. 2A-2F, the dissector tip 125 may comprise a sleeve 210 around at least a portion of the cannula 120. In some embodiments, the sleeve 210 may comprise one or more perforations 212 (e.g., one or more weakened portions or score lines) defining two or more portions 214 of the sleeve 210 proximate to the distal end 201 of the cannula 120. In some embodiments, the one or more perforations 212 may be separated by pulling the sleeve 210 away from the distal end 201 of the cannula 120 and toward the handle 110. In some embodiments, as shown in FIGS. 2C-2E, the separation at the one or more perforations or weakened portions 212 may result in the portions 214 of the sleeve 210 separating from one another.

In some embodiments, the separated portions 214 of the sleeve 210 may expose the opening 203 into the passage 202 of the cannula 120. In some non-limiting embodiments, the sleeve 210 may be comprised of a polymeric material, such as, for example and without limitation, PU (polyurethane), PVC (polyvinyl chloride), PTFE (Polytetrafluoroethylene).

In some embodiments, the sleeve 210 may be operatively connected to the actuator 140. In some embodiments, the sleeve 210 may be configured to be pulled along the cannula 120 from a closed position to an open position by sliding the slider knob 144 along the track 142 in a direction away from the cannula 120. In some embodiments, as shown in FIGS. 2A and 2B, when the sleeve 210 is in the closed position, the sleeve 210 may enclose the opening 203 of the distal end 201 of the cannula 120. In some embodiments, when the sleeve 210 is moved to the open position, the sleeve 210 may be pulled away from the distal end 201 of the cannula 120 and toward the handle 110. In some embodiments, as shown in FIGS. 2C-2F, moving the sleeve 210 toward the open position may separate the one or more perforations or weakened portions 212 and expose the opening 203 of the distal end 201 of the cannula 120. In some embodiments, when the sleeve 210 is pulled toward the handle 110 of the insertion tool 100, the distal end 201 of the cannula 120 may apply a sufficient amount of force against the sleeve to separate the portions 214 of the sleeve 210. In some embodiments, the sleeve 210 may be configured to be moved toward the open position before the cannula 120 moves toward the retracted position to ensure that the distal end 201 of the cannula 120 engages the portions 214 of the sleeve 210 with a sufficient amount of force to separate or rupture the perforations or weakened portions 212.

In some embodiments, as shown in FIGS. 2B-2F, the distal end 201 of the cannula 120 may be blunt-shaped. However, in other embodiments, the distal end 201 of the cannula 120 may form other shapes (e.g., a bevel shape) configured to create a tunnel and pocket below the skin surface.

Figure 2F:
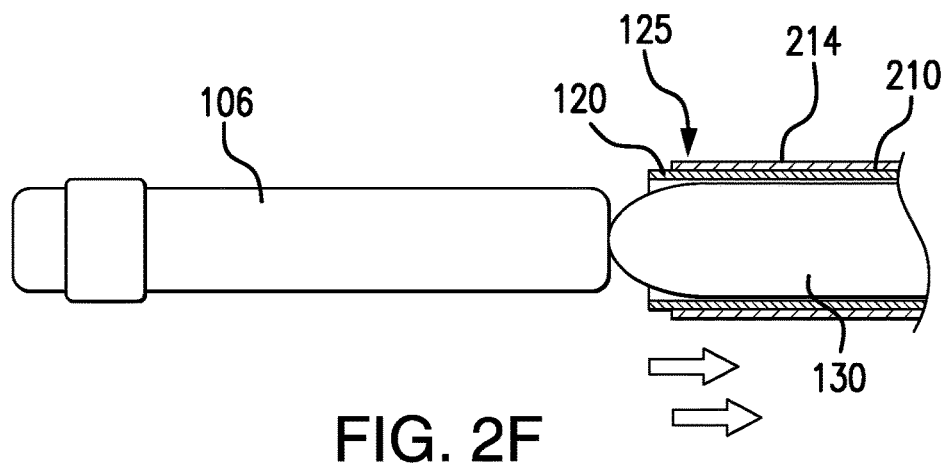
FIG. 2F is a cross-sectional side view of the dissector pull sleeve actuated tip in the open position with the push rod extended embodying aspects of the present disclosure.

In some embodiments, as shown in FIGS. 2B, 2D, and 2F, the rod 130 may be disposed, at least partially, in the passage 202 of the cannula 120. In some embodiments, the rod 130 may be configured to remain stationary (relative to the handle 110) in the passage 202 of the cannula 120 as the cannula 120 moves between the retracted position and the extended position. In some embodiments, as shown in FIG. 2B, when the cannula 120 is set at the extended position, the rod 130 may be spatially separated from the distal end 201 of the cannula 120 such that the passage 202 of the cannula 120 receives and/or holds the device 106 proximate to the distal end 201. In some embodiments, as shown in FIG. 2F, when the cannula 120 is set at the retracted position, the rod 130 may be disposed proximate the distal end 201 of the cannula 120 or may protrude through the distal end 201 of the cannula 120. In some embodiments, when the cannula 120 is moved from the extended position to the retracted position, the rod 130 may act as a backstop and force the device 106 through the opening 203 at the distal end 201 of the cannula 120 and at least partially out of the cannula 120.

In some embodiments, the rod 130 may be solid or hollow. In some embodiments, the rod 130 may be comprised of a rigid material, such as, for example and without limitation, stainless steel, polymeric material, such as ABS, Polycarbonate, Polyarylamide.

In some embodiments, the insertion tool 100 may create the subcutaneous pocket 102 below the skin surface 104 by inserting the cannula 120 at the extended position with the dissector tip 125 through an incision in the skin surface. In some embodiments, when the dissector tip 125 and the cannula 120 are inserted into the incision and while the dissector tip 125 and the cannula 120 create the subcutaneous pocket 102, the sleeve 210 may be set at the closed position (as shown in FIGS. 2A and 2B), and the sleeve 210 may enclose the device 106 in the passage 202 of the cannula 120. In some embodiments, after creating the subcutaneous pocket 102, the sleeve 210 may be moved (e.g., by pulling the sleeve 210 toward the handle 110) to the open position in which the opening 203 at the distal end 201 of the cannula 120 is exposed (as shown in FIGS. 2C and 2D). In some embodiments, after the moving the sleeve 210 to the open position, the insertion tool 100 may implant the device 106 by moving the cannula 120 from the extended position toward the retracted position. In some embodiments, as the cannula 120 moves toward the retracted position, the rod 130 may abut against the device 106, act as a backstop, and propel the device 106 through the opening 203 at the distal end 201 of the cannula 120, at least partially out of the cannula 120, and at least partially into the subcutaneous pocket 102 (as shown in FIGS. 2E and 2F). In some embodiments, after moving the cannula 120 to the retracted position (or simultaneously therewith), the handle 110 may be used to pull the cannula 120 out of the subcutaneous pocket 102, and the device 106 may be left in the subcutaneous pocket 102.

Figure 3A:
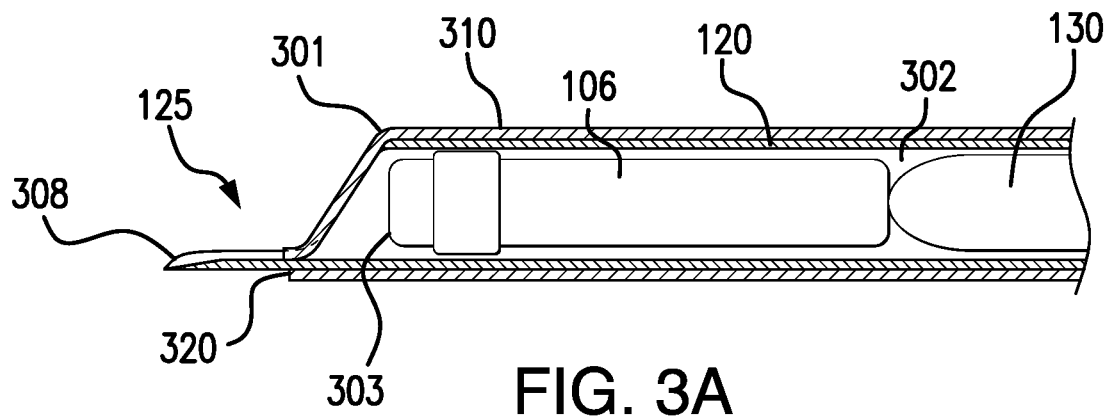
FIG. 3A is a cross-sectional side view of an insertion tool dissector pull sleeve actuated bevel-shaped tip in a closed position with the push rod retracted embodying aspects of the present disclosure.
Figure 3B:
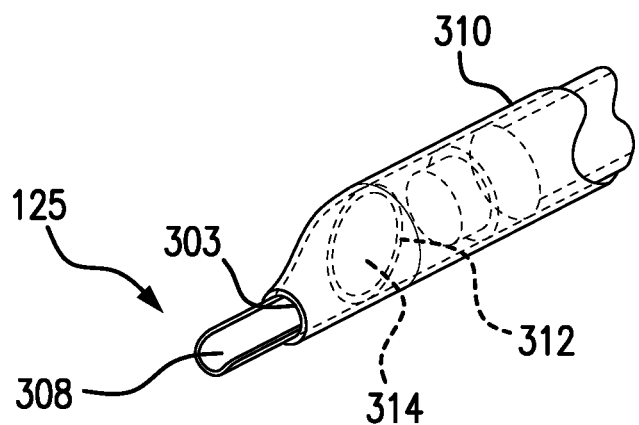
FIG. 3B is a perspective view of the insertion tool dissector pull sleeve actuated bevel-shaped tip in the closed position with the push rod retracted embodying aspects of the present disclosure.
Figure 3C:
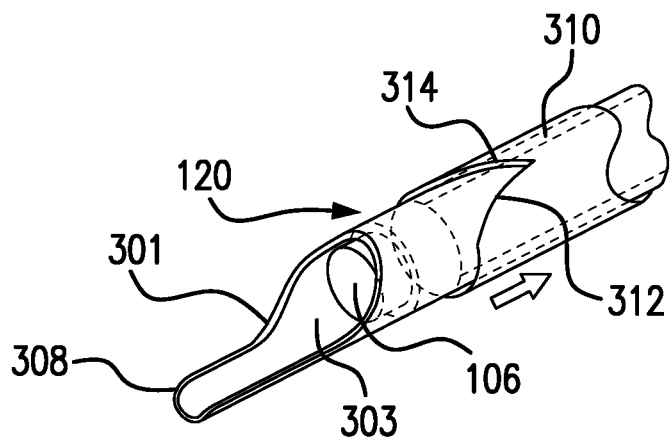
FIG. 3C is a perspective view of the insertion tool dissector pull sleeve actuated bevel-shaped tip in an open position with the push rod retracted embodying aspects of the present disclosure.

In some embodiments, as shown in FIGS. 3A-3C, the cannula 120 may have a bevel-shaped distal end 301. In some embodiments, the bevel-shaped distal end 301 may define an opening 303 into the passage 302 of the cannula 120. In some embodiments, the dissector tip 125 may include a protrusion 308 projecting from the distal end 301 of the cannula 120. In some non-limiting embodiments, the protrusion 308 and the cannula 120 may be formed from a single piece of a material.

In some embodiments, as shown in FIGS. 3A-C, the insertion tool 100 may further comprise a sleeve 310 at least partially around the cannula 120. In some embodiments, the sleeve 310 may enclose the opening 303 at the distal end 301 of the cannula 120. In some embodiments, the sleeve 310 may define an aperture 320 proximate to the distal end 301 of the cannula 120. In some embodiments, the dissector tip 125 (e.g., the protrusion 308) may project through the aperture 320 of the sleeve 310.

In some embodiments, the sleeve 310 may comprise a one or more perforations 312 (e.g., one or more weakened portions or score lines) defining two or more portions 314 of the sleeve 310 proximate to the distal end 301 of the cannula 120. In some embodiments, the one or more perforations 312 may be separated by pulling the sleeve 310 toward the handle 110. In some embodiments, as shown in FIG. 3C, the separation at the one or more perforations 312 may result in the portions 314 separating from one another. In some embodiments, the separated portions 314 of the sleeve 310 may expose the opening 303 into the passage 302 of the cannula 120.

In some embodiments, the sleeve 310 may be operatively connected to the actuator 140. In some embodiments, the sleeve 310 may be configured to be pulled along the cannula 120 from a closed position to an open position by sliding the slider knob 144 along the track 142 in a direction away from the cannula 120. In some embodiments, as shown in FIGS. 3A and 3B, when the sleeve 310 is in at the closed position, the sleeve 310 may enclose the opening 303 of the distal end 201 of the cannula 120. In some embodiments, as shown in FIG. 3C, when the sleeve 310 is moved to the open position, the sleeve 310 may be pulled toward the handle 110. In some embodiments, as shown in FIG. 3C, moving the sleeve 310 to the open position may separate the one or more perforations 312 and expose the opening 203 of the distal end 301 of the cannula 120. In some embodiments, when the sleeve 310 is pulled toward the handle 110 of the insertion tool 100, the distal end 301 of the cannula 120 and the device 106 may apply a sufficient amount of force against the aperture 320 of the sleeve 310 to separate the portions 314 of the sleeve 310. In some embodiments, the sleeve 310 may be configured to be moved toward the open position before the cannula 120 moves toward the retracted position to ensure that the distal end 301 of the cannula 120 engages the portions 314 of the sleeve 310 with a sufficient amount of force to separate or rupture the perforations or weakened portions 312.

In some embodiments, as shown in FIG. 3A, the rod 130 may be disposed, at least partially, in the passage 302 of the cannula 120. In some embodiments, the rod 130 may be configured remain stationary (relative to the handle 110) in the passage 302 of the cannula 120 as the cannula 120 moves between the retracted position and the extended position. In some embodiments, as shown in FIG. 3A, when the cannula 120 is set at the extended position, the rod 130 may be spatially separated from the distal end 301 of the cannula 120 such that the passage 302 of the cannula 120 may receive and/or hold the device 106 proximate to the distal end 301. In some embodiments, when the cannula 120 is set at the retracted position, the rod 130 may be disposed proximate the distal end 301 of the cannula 120 or protruding through the distal end 301 of the cannula 120. In some embodiments, moving the cannula from the extended position to the retracted position may force the device 106 through the opening 303 of the distal end 301 of the cannula 120.

In some embodiments, the insertion tool 100 may create the subcutaneous pocket 102 below the skin surface 104 by inserting the cannula 120 at the extended position with the dissector tip 125 through incision in the skin surface. In some embodiments, when the dissector tip 125 and the cannula 120 are inserted into the incision and while the dissector tip 125 and the cannula 120 create the subcutaneous pocket 102, the sleeve 310 may be set at the closed position (as shown in FIGS. 3A and 3B) and may enclose the device 106 in the passage 302 of the cannula 120. In some embodiments, after creating the subcutaneous pocket 102, the sleeve 310 may be moved (e.g., by pulling the sleeve 310 toward the handle 110) to the open position in which the opening 303 at the distal end 301 of the cannula 120 is exposed (as shown in FIG. 3C). In some embodiments, after the moving the sleeve 310 to the open position, the insertion tool 100 may implant the device 106 by moving the cannula 120 from the extended position toward the retracted position. In some embodiments, as the cannula 120 moves toward the retracted position, the rod 130 may abut against the device 106, act as a backstop, and propel the device 106 through the opening 303 at the distal end 301 of the cannula 120, at least partially out of the cannula 120, and at least partially into the subcutaneous pocket 102. In some embodiments, after moving the cannula 120 to the retracted position (or simultaneously therewith), the handle 110 may be used to pull the cannula 120 out of the subcutaneous pocket 102, and the device 106 may be left in the subcutaneous pocket 102.

Figure 4:
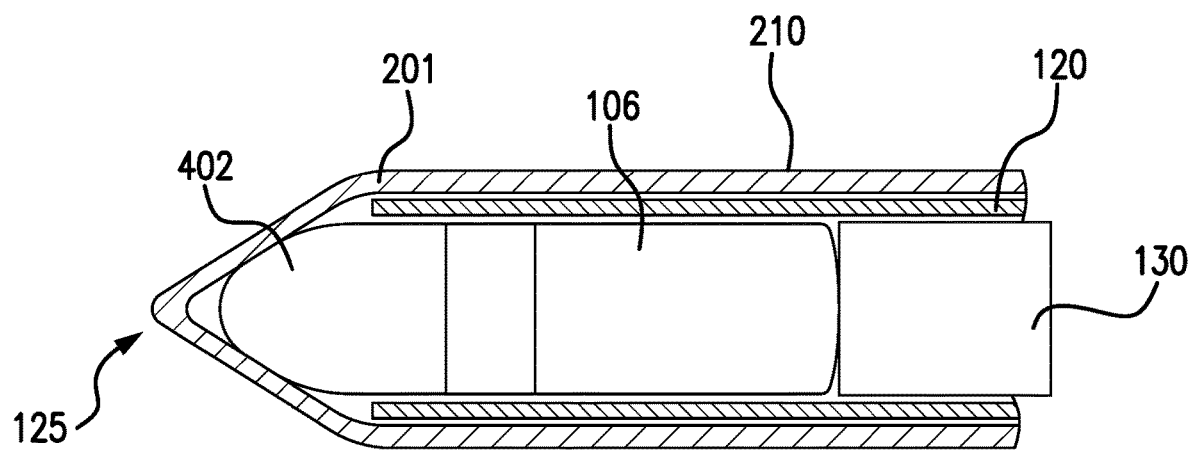
FIG. 4 is a cross-sectional side view of an insertion tool dissector device-supported tip in a closed position with the push rod retracted embodying aspects of the present disclosure.
Figure 5:
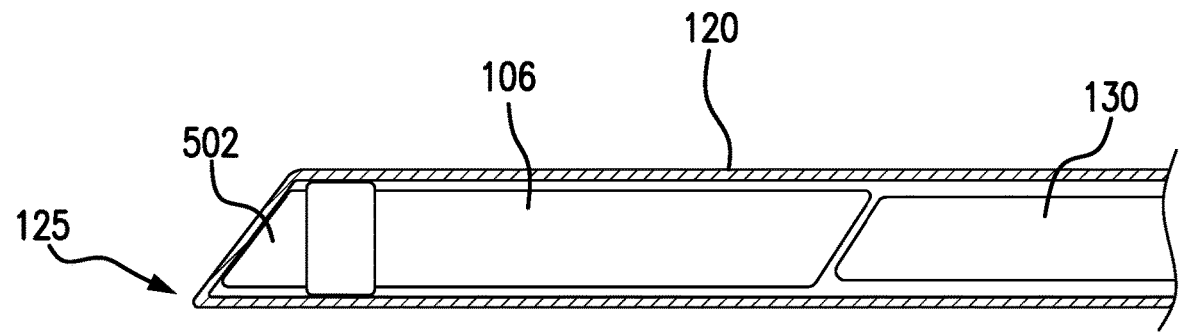
FIG. 5 is a cross-sectional side view of an insertion tool dissector device-supported bevel-shaped tip in a closed position with the push rod retracted embodying aspects of the present disclosure.

In some embodiments, as shown in FIGS. 4 and 5, the device 106 may support the dissector tip 125 (e.g., a portion of the surface-area of the device 106 may contact the dissector tip 125) when the cannula 120 is at the extended position. In some embodiments, the device 106 may support the dissector tip 125 when the dissector tip 125 and cannula 120 at the extended position are inserted into the incision in the skin surface 104 and create the subcutaneous pocket 102. In some embodiments, as shown in FIG. 4, a front end 402 of the device 106 may support a sleeve 201 when the sleeve 201 is in a closed position in which the sleeve 201 encloses the opening at the distal end of the cannula 120. In some non-limiting embodiments, as shown in FIG. 4, the device 106 may have a round edge that approximates the shape of the sleeve 201 of the dissector tip 125 that covers a blunt-shaped opening at the distal end of the cannula 210. In some alternative embodiments, as shown in FIG. 5, a front end 502 of the device 106 may support a sleeve when the sleeve is in a closed position in which the sleeve encloses the opening at the distal end of the cannula 120. In some non-limiting embodiments, as shown in FIG. 5, the device 106 may have a beveled edge that approximates a bevel-shape of the dissector tip 125.

Figure 6A:
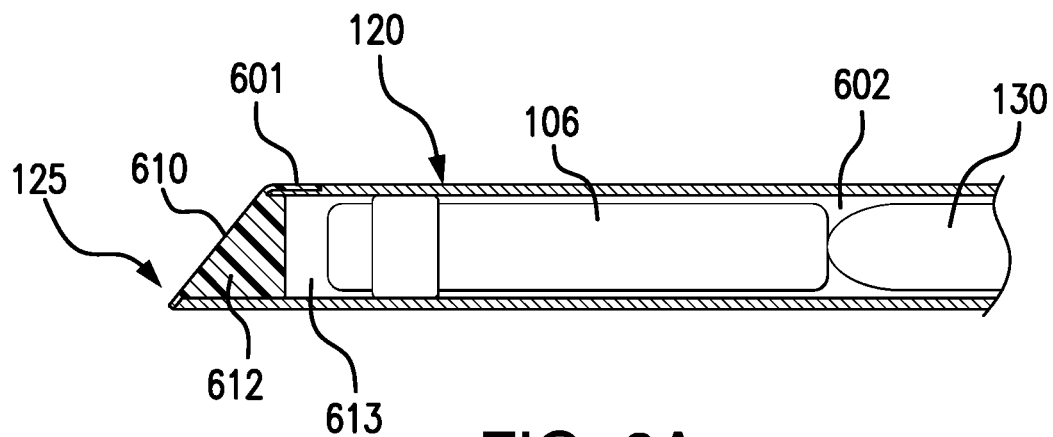
FIG. 6A is a cross-sectional side view of an insertion tool dissector plug-covered bevel-shaped tip in the closed and retracted position embodying aspects of the present disclosure.
Figure 6B:
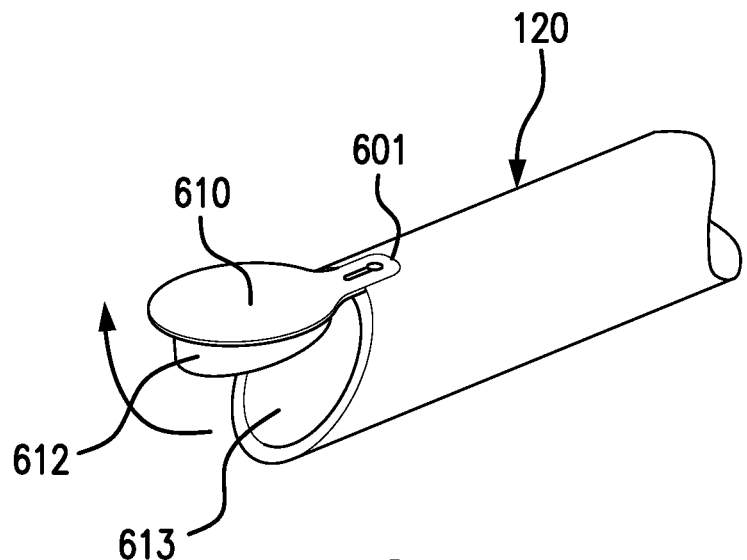
FIG. 6B is a perspective view of the insertion tool dissector plug-covered bevel-shaped tip in an open position with the push rod retracted embodying aspects of the present disclosure.

Referring to FIGS. 6A and 6B, in some embodiments, the cannula 120 may include a bevel-shaped distal end 601. In some embodiments, the bevel-shaped distal end 601 may define an opening 613 into the passage 602 of the cannula 120. In some non-limiting embodiments, the cannula 120 may be operatively connected to the actuator 140. In some embodiments, the cannula 120 may be configured to be moved from the extended position to the retracted position by sliding the slider knob 144 along the track 142 in a direction away from the cannula 120.

In some embodiments, the dissector tip 125 may include a flap 610 coupled to the cannula 120. In some embodiments, the flap 610 may pivot between a closed position and an open position. In some embodiments, when in a closed position, the flap 610 may abut against the distal end 601 of the cannula 120 and enclose the opening 613 at the distal end 601 of the cannula 120. In some embodiments, when in an open position, the flap 610 may be spatially separated from the distal end 601 and expose the opening 613 at the distal end 601 of the cannula 120. In some embodiments, the flap 610 may be configured to pivot from the closed position to the open position upon the application of force, by an object, such as the device 106, moving in an axial direction against the flap 610.

In some embodiments, as shown in FIGS. 6A and 6B, the flap 610 may include an extension 612 projecting from an interior surface of the flap 610. In some embodiments, when the flap 610 is in the closed position, the extension 612 may engage the interior surface of the cannula 120 to ensure that the flap 610 encloses the opening 613 of the distal end 601.

In some embodiments, as shown in FIG. 6A, the rod 130 may be disposed, at least partially, in the passage 602 of the cannula 120. In some embodiments, the rod 130 may be configured to remain stationary (relative to the handle 110) in the passage 613 of the cannula 120 as the cannula 120 moves between the retracted position and the extended position In some embodiments, as shown in FIG. 6A, when the cannula 120 is set at the extended position, the rod 130 may be spatially separated from the distal end 601 of the cannula 120 such that the passage 602 of the cannula 120 may receive and/or hold the device 106 proximate to the distal end 601. In some embodiments, when the cannula 120 is set at the retracted position, the rod 130 may be disposed proximate the distal end 601 or protruding through the distal end 601 of the cannula 120. In some embodiments, when the cannula 120 moves from the extended position to the retracted position, the rod 130 may force the device 106 through the opening 613 of the distal end 601 of the cannula 120.

In some embodiments, the insertion tool 100 may create the subcutaneous pocket 102 below the skin surface 104 by inserting the cannula 120 at the extended position with the dissector tip 125 through an incision in the skin surface. In some embodiments, when the dissector tip 125 and the cannula 120 are inserted into the incision and while the dissector tip 125 and cannula 120 create the subcutaneous pocket 102, the flap 610 may be in the closed position (as shown in FIG. 6A). In the closed position, the flap 610 may enclose the device 106 in the passage 602 of the cannula 120. In some embodiments, after creating the subcutaneous pocket 102, the insertion tool 100 may implant the device 106 by moving the cannula 120 toward the retracted position. In some embodiments, as the cannula 120 moves toward the retracted position, the rod 130 may abut against the device 106 to force the device 106 against the flap 610. In some embodiments, forcing the device 106 against the flap 610 may cause the flap 610 to pivot from the closed position to the open position (as shown in FIG. 6B). In some embodiments, the device 106 may then be pushed through the opening 613 at the distal end 601 of the cannula 120, at least partially out of the cannula 120, and at least partially into the subcutaneous pocket 102. In some embodiments, after moving the cannula 120 to the retracted position (or simultaneously therewith), the handle 110 may be used to pull the cannula 120 out of the subcutaneous pocket 102, and the device 106 may be left in the subcutaneous pocket 102.

Figure 7A:
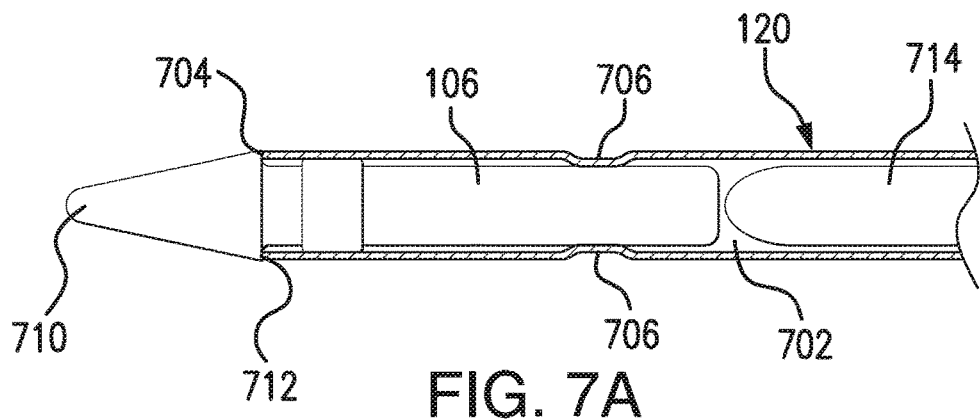
FIG. 7A is a cross-sectional side view of an insertion tool dissector having a device as a nose cone and with the push rod in a retracted position embodying aspects of the present disclosure.
Figure 7B:
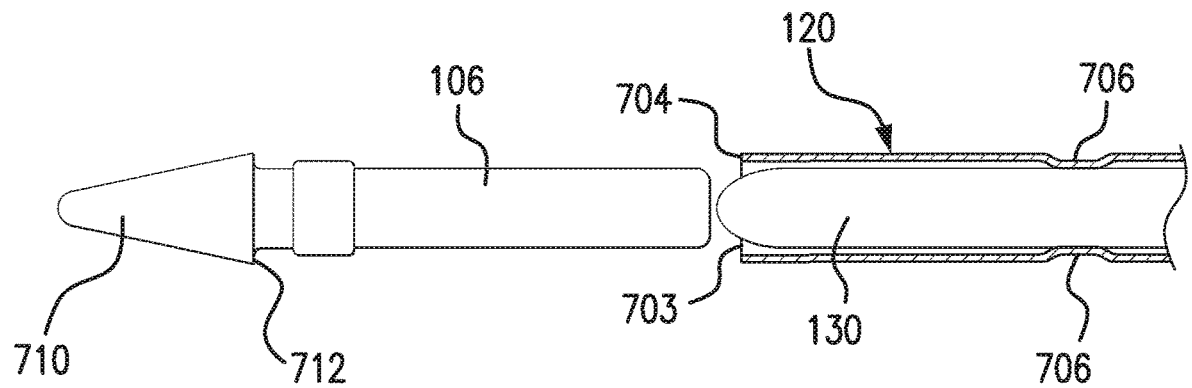
FIG. 7B is a cross-sectional side view of the insertion tool dissector having the device as the nose cone with the push rod in an extended position embodying aspects of the present disclosure.
Figure 7C:
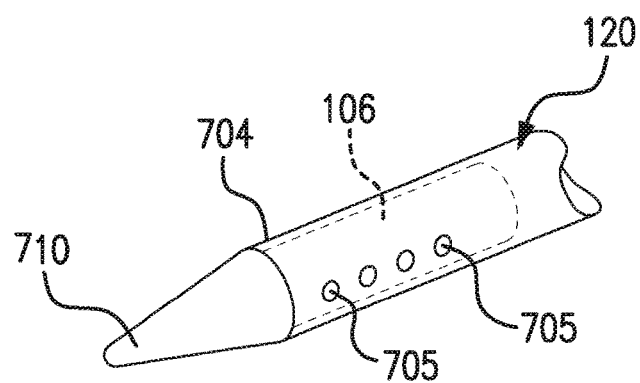
FIG. 7C is a perspective view of the insertion tool dissector having the device as the nose cone with the push rod in the retracted position embodying aspects of the present disclosure.

In some embodiments, as shown in FIGS. 7A-7C, the cannula 120 may define a passage 702 extending along a longitudinal axis thereof. In some non-limiting embodiments, the cannula 120 is operatively connected to the actuator 140. In some embodiments, the cannula 120 may be configured to be moved from the extended position to the retracted position by sliding the slider knob 144 along the track 142 in a direction away from the cannula 120. In some embodiments, the cannula 120 may include a distal end 704 defining an opening 703 into the passage 702. In some embodiments, when set at the extended position, the cannula 120 may be configured to retain and hold at least a portion of the device 106 in the passage 702 proximate to the open distal end 704. In some embodiments, the cannula 120 may comprise one or more flexible fingers 706 disposed along the cannula 120. In some embodiments, the one or more flexible fingers 706 may be configured to retain the device 106 by flexing toward the longitudinal axis of the cannula 120. In some embodiments, the flexible fingers 706 may be defined by a pair of parallel slits cut along the cannula 120, and each flexible finger 706 may include a strip of the dissector rod 120 defined by the pair of slits.

In some embodiments, as shown in FIGS. 7A-7C, the dissector tip 125 may be integrally connected to the device 106. In some embodiments, the dissector tip 125 may be a cone-shaped projection 710 disposed at a front end of the device 106. In some embodiments, when the device 106 is partially retained in the passage 702 of the cannula 120, the projection 710 of the device 106 protrudes out of the distal end 704 of the dissector rod 120. In some embodiments, projection 710 may include one or more shoulders 712 projecting from a side of the device 106 in a radial direction. In some embodiments, when the device 106 may be retained in the passage 702 of the cannula 120, the distal end 702 of the cannula 120 may abut against the shoulders 712, thereby ensuring that the projection 710 extends away from the distal end 704 by a predetermined length.

In some embodiments, as shown in FIGS. 7A and 7B, the rod 130 may be disposed, at least partially, in the passage 702 of the cannula 120. In some embodiments, the rod 130 may be configured to remain stationary (relative to the handle 110) in the passage 702 of the cannula 120 as the cannula 120 moves between the retracted position and the extended position. In some embodiments, as shown in FIG. 7A, when the cannula 120 is set at the extended position, the rod 130 may be spatially separated from the distal end 704 of the cannula 120 such that the passage 702 of the cannula 120 may receive at least a portion of the device 106 proximate to the distal end 704. In some embodiments, when the cannula 120 is set at the retracted position, the rod 130 may be disposed proximate the distal end 704 or protruding through the distal end 704 of the cannula 120. In some embodiments, when the cannula 120 is moved from the extended position to the retracted position, the rod 130 may force the device 106 through the opening 703 at the distal end 704 of the cannula 120 and at least partially out of the cannula 120.

In some embodiments, as shown in FIG. 7C, the cannula 120 may further comprise one or more ports 705 for introducing a hydration fluid (e.g., saline fluid) into the passage 702. In some embodiments, the hydration fluid may be introduced into the one or more ports 705 as device 106 is held in the passage 702 of the cannula 120. In some embodiments, the hydration fluid may hydrate (or at least begin hydration of) at least a portion of the device 106 before implantation of the device 106. For example, for a non-limiting embodiment of a device 106 that is an analyte sensor, the analyte sensor may include an analyte indicator including a hydrogel, and the hydration fluid may hydrate (or at least begin hydration of) at least the analyte indicator of the sensor before insertion. In some non-limiting embodiments, the device 106 may require hydration before the device 106 can operate normally. Accordingly, in some embodiments, hydration fluid in the cannula 120 may reduce or eliminate an amount of time that the device 106 is required to be implanted in the body before device 106 operates normally.

In some embodiments, the insertion tool 100 may create the subcutaneous pocket 102 below the skin surface 104 by inserting the cannula 120 at the extended position with the dissector tip 125 through an incision in the skin surface. In some embodiments, when the cannula 120 is inserted into the incision and while the projection 710 and the cannula 120 create the subcutaneous pocket 102, the device 106 may be partially held in the passage 702 of the cannula 120 with the projection 710 protruding away from the distal end 704 of the cannula 120. In some embodiments, after creating the subcutaneous pocket 102, the insertion tool 100 may implant the device 106 by moving the cannula 120 toward the retracted position. In some embodiments, as the cannula 120 moves toward the retracted position, the rod 130 may abut against the device 106, act as a backstop, and propel the device 106 through the opening 703 at the distal end 701 of the cannula 120, at least partially out of the cannula 120, and at least partially into the subcutaneous pocket 102 (as shown in FIG. 7B). In some embodiments, after moving the cannula 120 to the retracted position (or simultaneously therewith), the handle 110 may be used to pull the cannula 120 out of the subcutaneous pocket 102, and the device 106 may be left in the subcutaneous pocket 102.

Figure 8A:
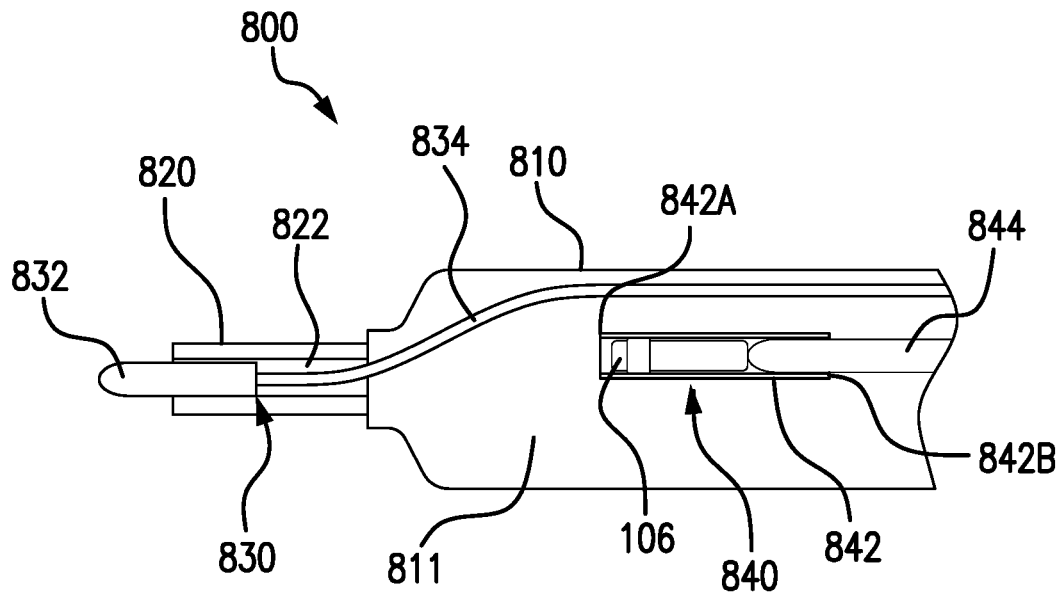
FIG. 8A is a cross-sectional side view of an insertion tool with the dissector tip set in the extended position and the cannula set in the retracted position embodying aspects of the present disclosure.
Figure 8B:
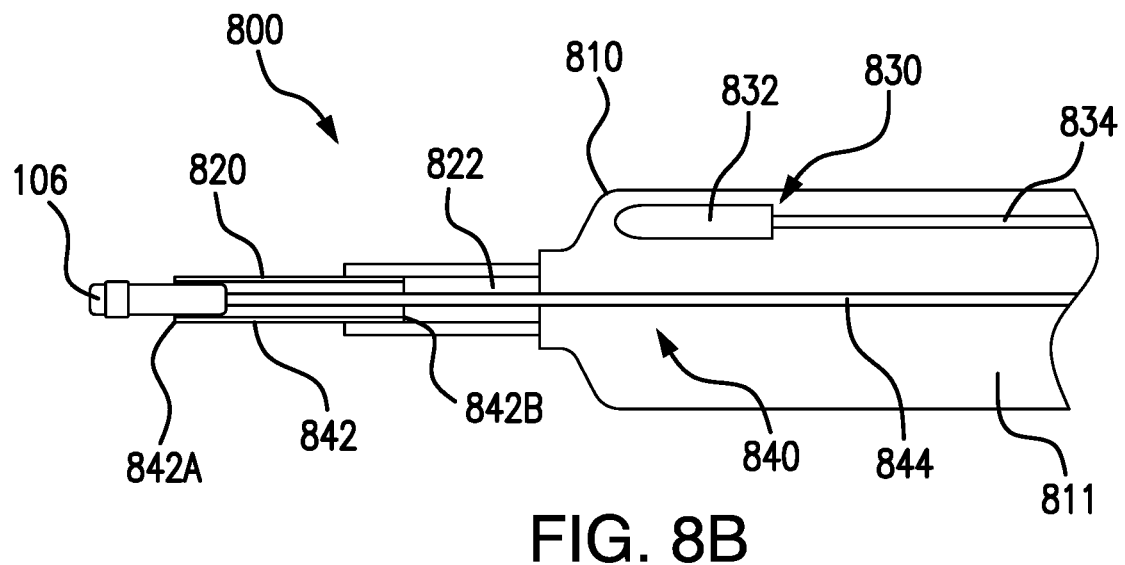
FIG. 8B is a cross-sectional side view of an insertion tool with the dissector tip set in the retracted position and the cannula set in the extended position embodying aspects of the present disclosure.

FIGS. 8A and 8B illustrate an exemplary insertion tool 800 for creating the subcutaneous pocket 102 below the skin surface 104 and implanting the device 106 in the subcutaneous pocket 102. In some embodiments, the insertion tool 800 may include a handle 810, a tunneling tube 820, a dissector 830, an inserter 840, and one or more actuators (not shown). In some embodiments, the handle 810 may define a cavity 811 therein. In some embodiments, the tunneling tube 820 may extend from a first end 812 of the handle 810 and may define a passage 822 opening into the cavity 811 of the handle 810.

In some embodiments, the tunneling tube 820 may be configured to move in an axial direction between an extended position and a retracted position. In some embodiments, when the tunneling tube 820 is set at the extended position, the tunneling tube 820 and the dissector 830 may be configured to create the subcutaneous pocket 102 below the skin surface 104. In some embodiments, when the tunneling tube 820 is moved to the retracted position, the tunneling tube 820 and the inserter 840 may be configured to deploy the device 106 into the subcutaneous pocket 102. In some embodiments, when the tunneling tube 820 is set at the extended position, a substantial portion of the tunneling tube 820 may be disposed outside the handle 110. In some embodiments, when the tunneling tube 820 is set at the retracted position, a portion or all of the tunneling tube 820 may be disposed in a cavity 811 of the handle 810.

In some embodiments, the dissector 830 may comprise a first rod 834 disposed at least partially in the cavity 811 of the handle 810. In some embodiments, the first rod 834 may be rigid. However, this is not required, and, in some alternative embodiments, the first rod 834 may be flexible. In some embodiments, the first rod 834 may comprise of a polymeric material, such as nylon, polypropylene, or polyvinylchloride. In some embodiments, a dissector tip 832 may be coupled to a distal end of the first rod 834. In some embodiments, the dissector tip 832 and the first rod 834 may be configured to move between an extended position and a retracted position. FIGS. 8A and 8B show the dissector tip 832 and the first rod 834 in the extended and retracted positions, respectively. In some non-limiting embodiments, as shown in FIG. 8A, when at the extended position, the dissector tip 832 may protrude out of a distal end of the tunneling tube 820. In some embodiments, the dissector tip 832 may be configured to create the subcutaneous pocket 102 below the skin surface 104. In some embodiments, as shown in FIG. 8B, when set at the retracted position, the dissector tip 832 may be disposed in the cavity 811 of the handle 810.

In some embodiments, the first rod 834 may be operatively connected to an actuator, and the actuator may be configured to move the first rod 834 and the dissector tip 832 between the extended and retracted positions. In some embodiments, the actuator may be configured to move the dissector tip 832 out of the tunneling tube 820 and into the cavity 811. In some embodiments, the actuator may be a slider or a lever connected to the first rod 834. In some embodiments, the actuator may be a spring loaded mechanism connected to the first rod 834 to advance and retract the first rod 834. Although some embodiments include an actuator configured to move the first rod 834 and the dissector tip 832 between extended and retracted positions, this actuator is not required, and, in some alternative embodiments, a user may move the first rod 834 and the dissector tip 832 from the extended position shown in FIG. 8A to the retracted position shown in FIG. 8B by pulling directly on the first rod 832.

In some embodiments, the inserter 840 may comprise a second rod 844 disposed at least partially in the cavity 811 of the handle 810. In some embodiments, the second rod 844 may be rigid. However, this is not required, and, in some alternative embodiments, the second rod 844 may be flexible. In some embodiments, the inserter 840 may include a cannula 842. In some embodiments, the cannula 842 may include a first end 842A configured to hold and release the device 106. In some embodiments, the cannula 842 may include a second end 842B coupled to a distal end of the second rod 844. In some embodiments, the second rod 844 may be configured to move along the cavity 811 of the handle 810. In some embodiments, the cannula 842 may be configured to move between a retracted position and an extended position. In some embodiments, the cannula 842 may be configured to slide along the second rod 844 toward the retracted position, as the tunneling tube 820 moves toward the retracted position.

FIGS. 8A and 8B show the cannula 842 in the retracted and extended positions, respectively. In some embodiments, as shown in FIG. 8A, when at the retracted position, the cannula 842 may be disposed in the cavity 811 of the handle 810. In some embodiments, as shown in FIG. 8B, when at the extended position, the cannula 842 may be at least partially disposed in the passage 822 of the tunneling tube 820. In some embodiments, the tunneling tube 820 may hold the cannula 842 in place at its extended position. In some embodiments, when the cannula 842 is at its extended position and at least partially disposed in the tunneling tube 820, the tunneling tube 820 may retract in axial direction toward the handle 810, which may also slide the cannula 842 back toward the handle 810. In some embodiments, as the cannula 842 retracts with the tunneling tube 820 into the cavity 811 of the handle 810, the second rod 844 may remain in an extended position and abut against the device 106 to force the device 106 at least partially out of the cannula 842 and the tunneling tube 820 and at least partially into the subcutaneous pocket 102.

In some embodiments, the second rod 844 may be operatively connected to an actuator, and the actuator may be configured to move the second rod 844, the cannula 842, and the tunneling tube 820 between retracted and extended positions. In some embodiments, the actuator configured to move the second rod 844, the cannula 842, and the tunneling tube 820 between retracted and extended positions may be the same actuator that is configured to move the first rod 834 and the dissector tip 832 between retracted and extended positions. In some embodiments, the actuator may be a slider knob (not shown) configured to slide along a track (not shown) disposed along the handle 810. In some embodiments, the actuator may include a fork (not shown) extending from the slider knob and comprising a plurality of prongs connected to the first rod 834 and the second rod 844. In some embodiments, the actuator may include a catch mechanism (not shown), such as a strut, to hold the second rod 844 in the extended position, while the actuator moves the tunneling tube 820 and the cannula 842 toward the retracted position. In some alternative embodiments, a first actuator may be configured to move the second rod 844 and the cannula 842 between retracted and extended positions, and a different, second actuator may be configured to move the first rod 834 and the dissector tip 832 between retracted and extended positions.

In some embodiments, the insertion tool 800 may create the subcutaneous pocket 102 below the skin surface 104 by setting the dissector 830 in the extended position (as shown in FIG. 8A) and inserting the tunneling tube 820 with the dissector tip 832 protruding from the tunneling tube 820 through an incision in the skin surface. In some embodiments, after creating the subcutaneous pocket 102, the dissector tip 832 and first rod 834 may be moved from their extended position to their retracted position. In some embodiments, the second rod 844 and cannula 842 may then be moved from the retracted position toward the extended position so that the cannula 842 (with the device 106 held therein) is disposed at least partially in the tunneling tube 820. In some embodiments, with the cannula 842 disposed at least partially in the tunneling tube 820, the tunneling tube 820 may be retracted toward the handle 810 to slide the cannula 842 along the second rod 844 and at least partially into the cavity 811 of the handle 810. In some embodiments, as the cannula 842 retracts with the tunneling tube 820 into the cavity 811 of the handle 810, the second rod 844 may remain in the extended position (e.g., using the catch mechanism of the actuator 950) and abut against the device 106 to force the device 106 at least partially out of the cannula 842 and the tunneling tube 820. In some embodiments, the handle 810 may be used to pull the tunneling tube 820 out of the subcutaneous pocket 102, and the device 106 may be left in the subcutaneous pocket 102. In some embodiments, one or more of the dissector tip 832, first rod 834, cannula 842, and second rod 844 may be moved while keeping the tunnel tube 820 disposed in the subcutaneous pocket 102.

Figure 9A:
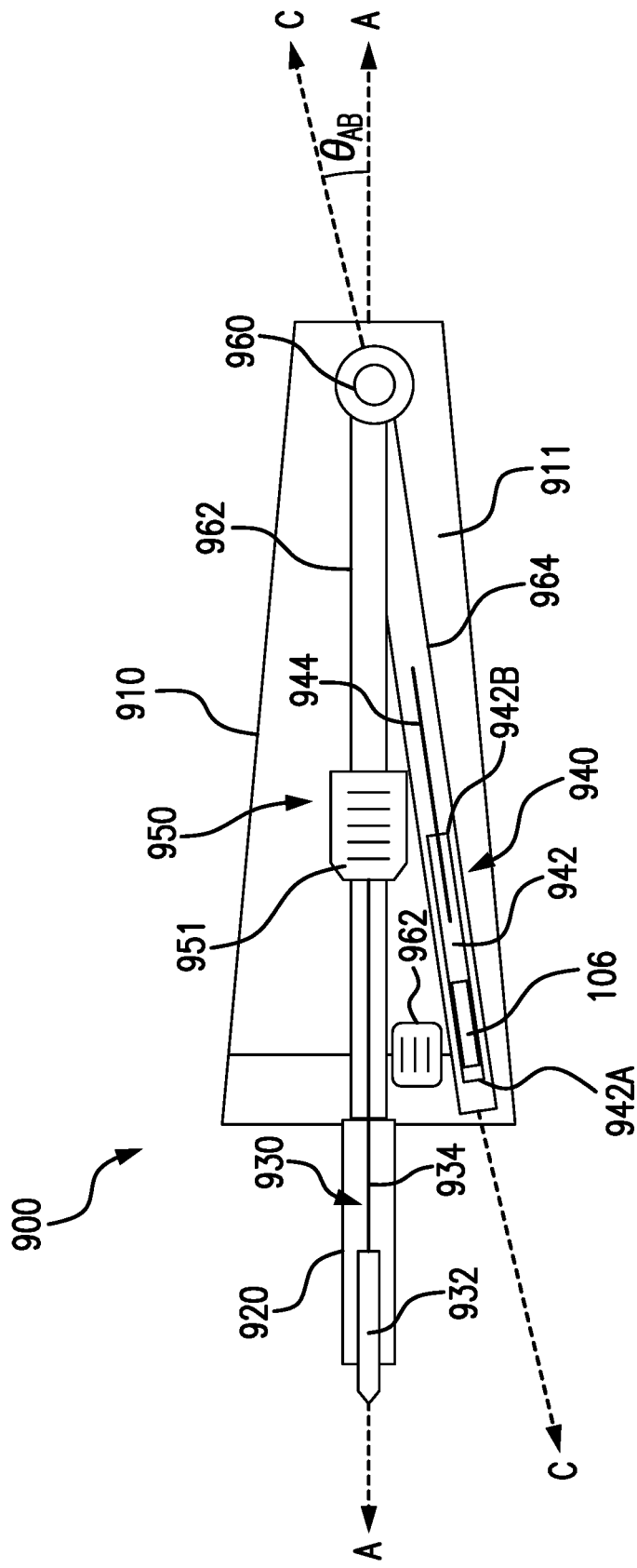
FIG. 9A is a schematic view of an insertion tool with the dissector tip set in the extended position and the cannula set in the retracted position embodying aspects of the present disclosure.
Figure 9B:
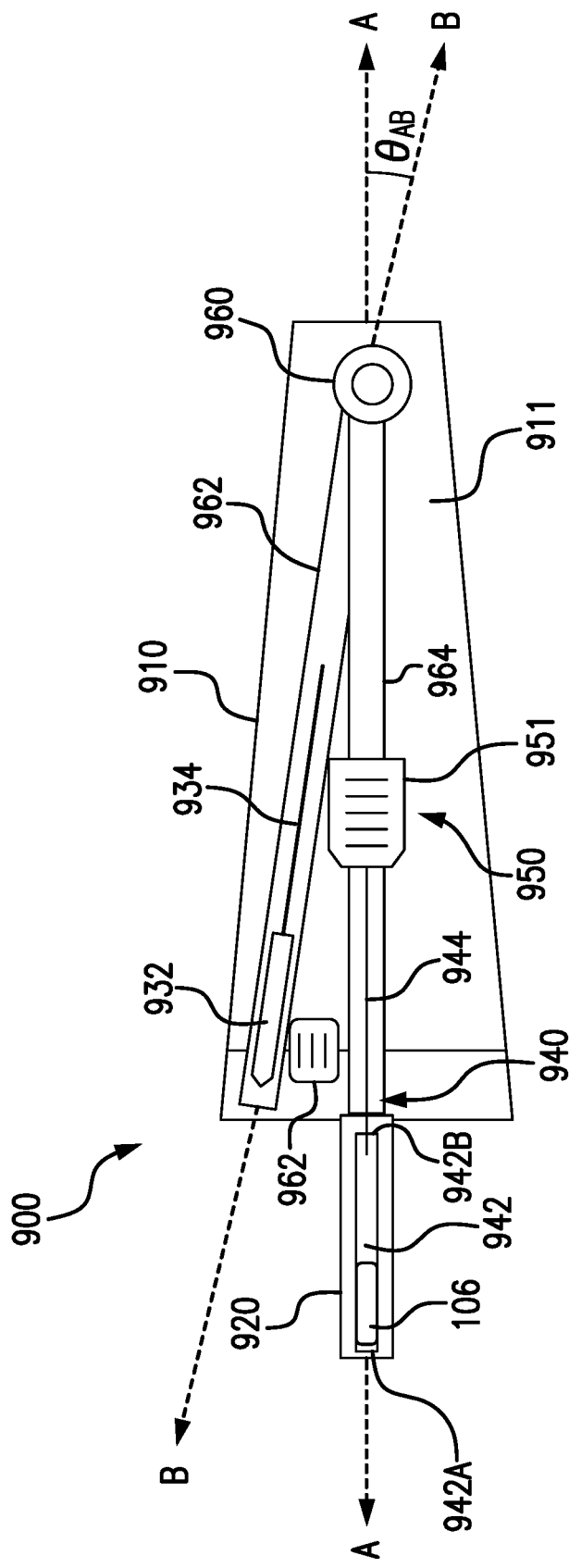
FIG. 9B is a schematic view of an insertion tool with the dissector tip set in the retracted position and the cannula set in the extended position embodying aspects of the present disclosure.

FIGS. 9A and 9B illustrate an exemplary insertion tool 900 for creating the subcutaneous pocket 102 below the skin surface 104 and implanting the device 106 in the subcutaneous pocket 102. In some embodiments, the insertion tool 900 comprises a handle 910, a tunneling tube 920, a dissector 930, an inserter 940, and an actuator 950.

In some embodiments, the insertion tool 900 may include one or more of the same features as the embodiment of the insertion tool 800 shown in FIG. 8. For example, the tunneling tube 920 may be configured to move between an extended position to create the subcutaneous pocket 102 using the dissector 930 and a retracted position to deploy the device 106 into the subcutaneous pocket 102 using the inserter 940. In some embodiments, the dissector 930 may include a first rod 934 configured to move along a cavity 911 of the handle 810 and a dissector tip 932 coupled to a distal end of the first rod 934. In some embodiments, the inserter 940 may include a second rod 944 configured to move along the cavity 911 of the handle 810 and a cannula 942 configured to hold the device 106 at a first end 942A and coupled to the second rod 944 at a second end 942B.

In some embodiments, as shown in FIGS. 9A and 9B, the dissector 930 may be configured to pivot from an operating position disposed along a first axis A defined by the tunneling tube 920 to an idle position disposed along a second axis B. In some embodiments, the second axis B may extend at an acute angle $\theta_{AB}$ (e.g., 10°) with respect to the first axis A. In some embodiments, the inserter 940 may be configured to pivot from an idle position disposed along a third axis C to an operating position disposed along the first axis A. In some embodiments, the third axis C may extend at an acute angle $\theta_{AC}$ (e.g., 10°) with respect to the first axis A.

In some embodiments, as shown in FIGS. 9A and 9B, the insertion tool 900 may further comprise a hinge 960. In some non-limiting embodiments, the hinge 960 may be disposed in the handle 910. In some embodiments, the hinge 960 may include a first arm 962 disposed in the cavity 911 and configured to pivot about an axis defined by the hinge 960 from the operating position extending along the first axis A to the idle position extending along the second axis B. In some embodiments, the hinge 960 may include a second arm 964 disposed in the cavity 911 and configured to pivot about an axis defined by the hinge 960 from the idle position extending along the third axis C to the operating position extending along the first axis A.

In some embodiments, the first arm 962 may define a passage, and the dissector tip 932 and the first rod 934 may be disposed in the passage of the first arm 962. In some embodiments, the dissector 930 may be configured to move between the operating and idle positions as the first arm 962 pivots about the hinge 960. In some embodiments, the dissector tip 932 and the first rod 930 may be configured to move along the passage of the first arm 962 between retracted and extended positions when the first arm 962 is set at the operating position extending along the first axis A. In some embodiments, the dissector tip 932 and the first rod 930 may be configured to remain stationary in the retracted position when the first arm 962 is set at the idle position extending along the second axis B.

In some embodiments, the second arm 964 may define a passage, and the cannula 942 and the second rod 944 may be disposed in the passage of the second arm 964 such that the inserter 940 may be configured to move between the idle and operating positions as the second arm 964 pivots about the hinge 960. In some embodiments, the cannula tube 942 and the second rod 944 may be configured to move along the passage of the second arm 964 is set at the operating position extending along the first axis A. In some embodiments, the cannula tube 942 and the second rod 944 may be configured to remain stationary in the retracted position when the second arm 964 is set at the idle position extending along the third axis C.

In some embodiments, the insertion tool 900 may include a pivot actuator 962 operatively connected to the dissector 930 and the inserter 940 to cause the pivoting movement of the dissector 930 and the inserter 940 between the idle and operating positions. In some embodiments, the pivot actuator 962 may include, for example and without limitation, a twist knob or a slider. In other embodiments (not shown), the insertion tool 900 may comprise other internal mechanisms (e.g. a spring-loaded device) to move the dissector 930 and the inserter 940 between the idle and operating positions.

In some embodiments, the actuator 950 may be disposed in the handle 910 and may be operatively connected to the tunneling tube 920, the dissector 930, and the inserter 940. In some embodiments, the actuator 950 may be configured to selectively force the tunneling tube 920, the dissector 930, and the inserter 940 to move between retracted and extended positions. In some embodiments, the actuator 950 may include a track (not shown) extending along the handle 910 and a slider knob 951 configured to slide along the track. In some embodiments, the actuator 950 may include a fork (not shown) extending from the slider knob 951 and configured to removably connect to the dissector 930 and inserter 940 when pivoted into the operating position. In some embodiments, the actuator 950 may include a catch mechanism (not shown), such as a strut, to hold the second rod 944 in the extended position, while the actuator 950 moves the tunneling tube 920 and the cannula 942 toward the retracted position.

In some embodiments, the insertion tool 900 may create the subcutaneous pocket 102 below the skin surface 104 by first setting the dissector 930 in the operating position (e.g., using the pivot actuator 962) and sliding the dissector tip 932 and the first rod 934 to the extended position (as shown in FIG. 9A) (e.g., using the actuator 950). In some embodiments, the subcutaneous pocket 102 may be created by inserting the tunneling tube 920 with the dissector tip 932 protruding from the tunneling tube 920 through an incision in the skin surface. In some embodiments, after creating the subcutaneous pocket 102, the dissector tip 932 and first rod 934 may be moved from their extended position to their retracted position. In some embodiments, the dissector 930 in the retracted position may be pivoted from the operating position along the first axis A to the idle position along the second axis B, and the inserter 940 may be pivoted from the idle position along the third axis C to the operating position along the first axis A (e.g., using pivot actuator 962). In some embodiments, the second rod 944 and cannula 942 of the inserter 940 in the operating position may then be moved from the retracted position toward the extended position (e.g., using the actuator 950) so that the cannula 942 (with the device 106 held therein) is disposed at least partially in the tunneling tube 920. In some embodiments, with the cannula 942 disposed at least partially in the tunneling tube 920, the tunneling tube 920 may be retracted toward the handle 910 (e.g., using the actuator 950) to slide the cannula 942 along the second rod 944 and into at least partially into the cavity 911 of the handle 910. In some embodiments, as the cannula 942 retracts with the tunneling tube 920 into the cavity 911 of the handle 910, the second rod 944 may remain in the extended position (e.g., using the catch mechanism of the actuator 950), abuts against the device 106, act as a backstop, and force the device 106 at least partially out of the cannula 942 and the tunneling tube 920. In some embodiments, after at least partially retracting the tunneling tube 920 into the cavity 911 of the handle 910 (or simultaneously therewith), the handle 910 may be used to pull the tunneling tube 920 out of the subcutaneous pocket 102, and the device 106 may be left in the subcutaneous pocket 102. In some embodiments, one or more of the dissector tip 932, first rod 934, cannula 942, second rod 944, actuator 950, and pivot actuator 962 may be moved while keeping the tunneling tube 920 disposed in the subcutaneous pocket 102.

Figure 10:
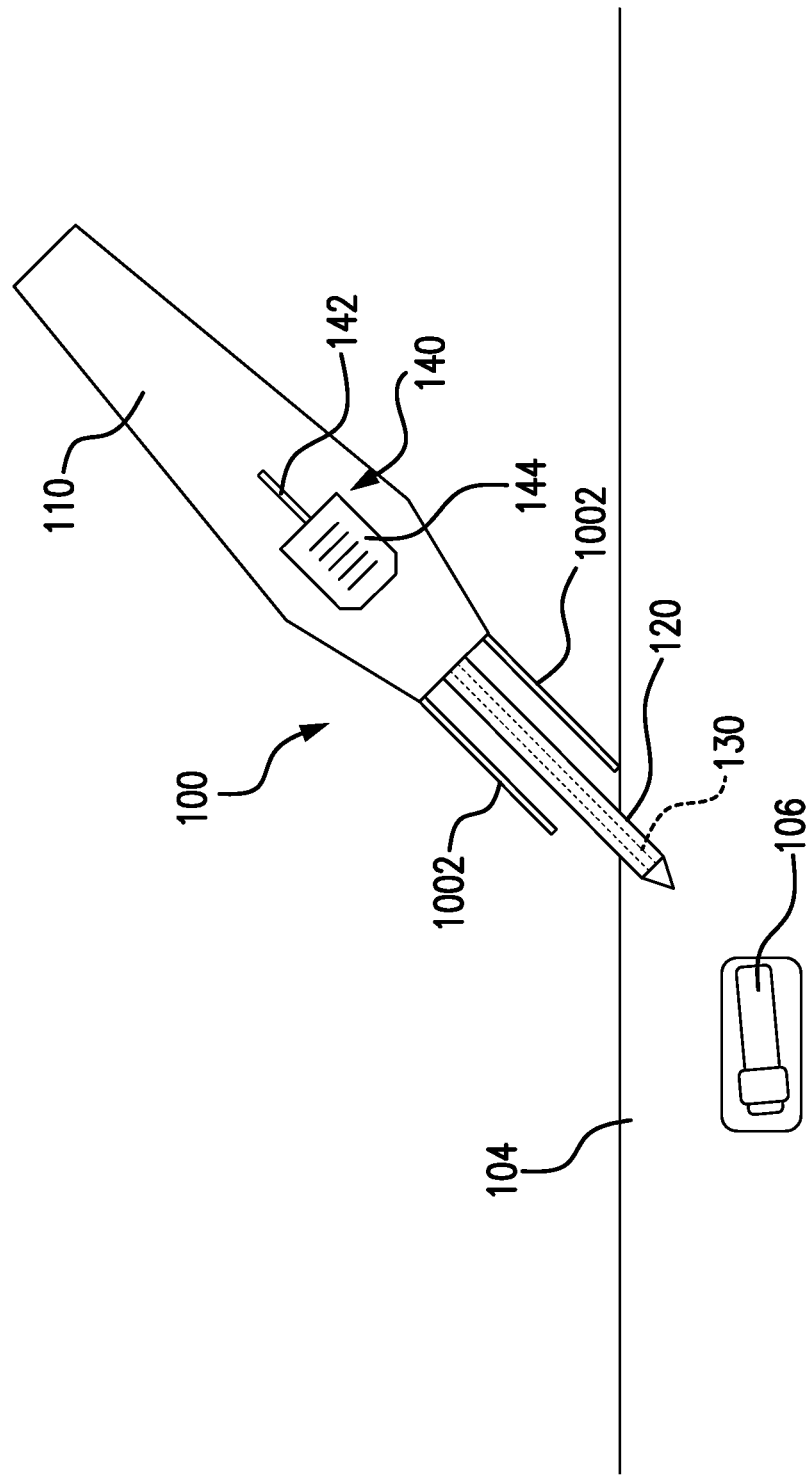
FIG. 10 is a schematic view of an insertion tool embodying aspects of the present disclosure.

FIG. 10 illustrates an exemplary insertion tool 1000, which may comprise any of the features described in FIGS. 1-7. In some embodiments, the insertion tool 1000 may include one or more guide prongs 1002 extending from a first end of the handle 110. In some embodiments, the one or more guide prongs 1002 may be configured to limit the depth at which the dissector rod 120 is capable of creating the subcutaneous pocket 102. In some embodiments, the dissector rod 120 may extend farther from the end of the handle 110 than the one or more guide prongs 1002.

In some embodiments, all the configurations of the insertion tools 100, 800, 900, and 1000 described herein may include a loading port disposed in the handle and in communication with the cannula for introducing a hydration fluid (e.g., saline fluid) into the cannula. In some embodiments, the hydration fluid may hydrate (or at least begin hydration of) at least a portion of the device 106 (e.g., an analyte indicator or hydrogel of the device 106) before implantation of the device 106.

Figure 11:
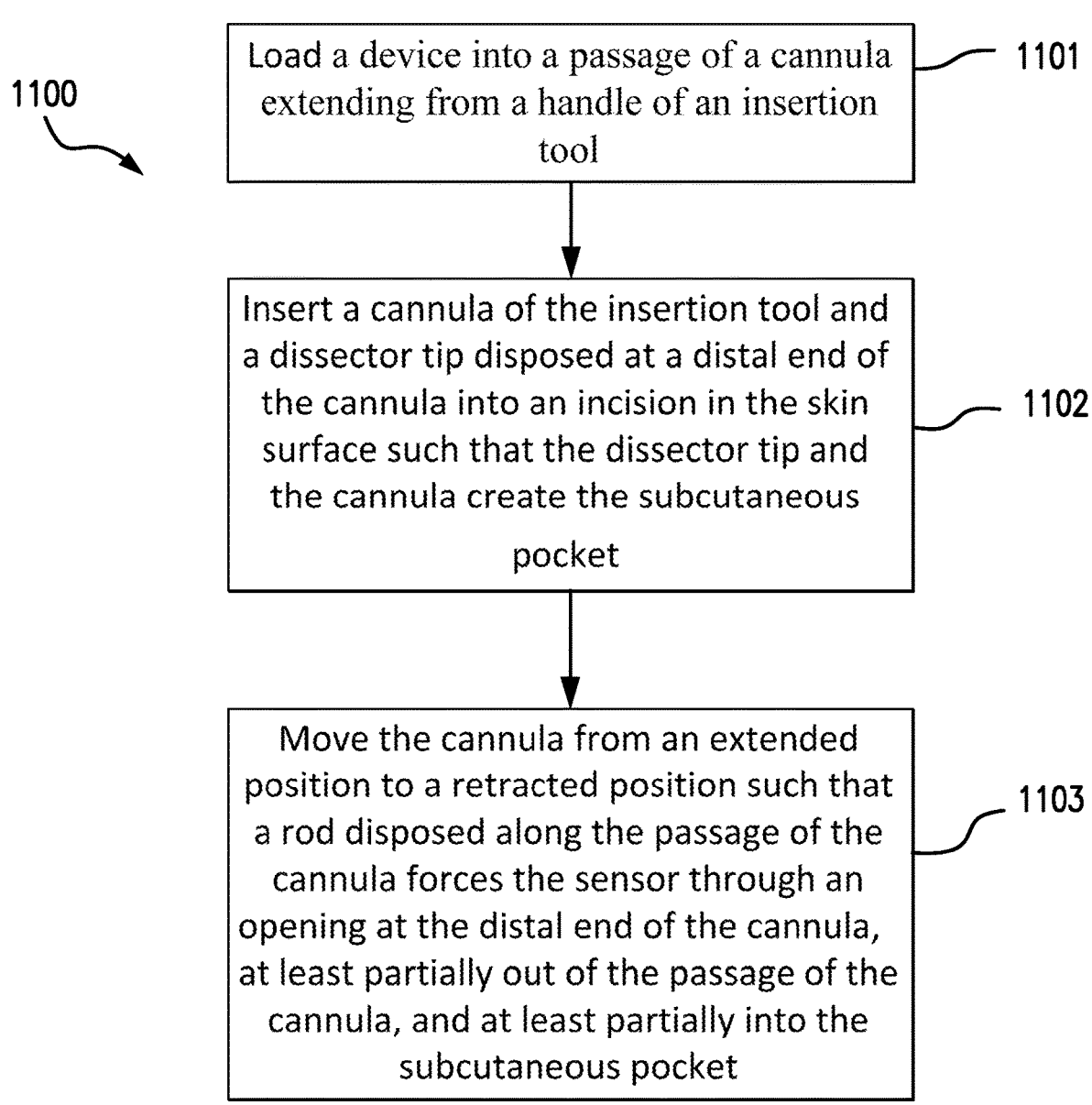
FIG. 11 is a flow chart of a method of creating a subcutaneous pocket and implanting a device in the subcutaneous pocket embodying aspects of the present disclosure.

FIG. 11 is a flow chart showing a method 1100 of creating a subcutaneous pocket below a skin surface and implanting a device in the subcutaneous pocket embodying aspects of the present disclosure. In some embodiments, the insertion tools 100, 800, 900, and 1000 described above in FIGS. 1-10 may be used to create the subcutaneous pocket and implant the device according to the method described in FIG. 11.

In some embodiments, the method 1100 may include a step 1101 of loading the device into a passage of a cannula extending from a handle of the insertion tool.

In some embodiments, the method 1100 may include a step 1102 of inserting a cannula of the insertion tool and a dissector tip disposed at a distal end of the cannula into an incision in the skin surface such that the dissector tip and the cannula create the subcutaneous pocket.

In some embodiments, the method 1100 may include a step 1103 of moving the cannula from an extended position to a retracted position such that a rod disposed along the passage of the cannula forces the device through an opening at the distal end of the cannula, out of the passage of the cannula, and into the subcutaneous pocket.

In some embodiments, the method 1100 may further include, after loading the device into the passage and before inserting the cannula and the dissector tip, a step of pulling a sleeve around the distal end of the cannula to enclose the opening in the distal end of the cannula. In some embodiments, the method 1100 may further include, before the step of loading, a step of pulling a sleeve received around the cannula toward the handle to expose the opening in the distal end of the cannula.

In some embodiments, the method 1100 may further include using an actuator disposed in the handle to move the cannula from the extended position to the retracted position. In some embodiments the method 1100 may further include pulling the cannula away from the subcutaneous pocket.

In some embodiments, the method 110 may further include a step of pulling a sleeve along the cannula from a closed position, in which the sleeve encloses the opening at the distal end of the cannula, to an open position, in which the sleeve exposes the opening at the distal end of the cannula.

In some embodiments, the insertion tool may further include a flap covering the opening at the distal end of the cannula. In some embodiments, the method 1100 may further include a step of moving the cannula from the extended position to the retracted position spatially separates the flap from the distal end of the cannula and exposes the opening at the distal end of the cannula.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. An insertion tool for creating a subcutaneous pocket below a skin surface and implanting a device in the subcutaneous pocket, the insertion tool comprising:
   a handle defining a cavity therein;
   a tunneling tube extending from a first end of the handle and defining a passage opening into the cavity of the handle, and the tunneling tube is configured to move in an axial direction between an extended position and a retracted position;
   a dissector comprising a blunt tip configured to move between a retracted position, wherein the blunt tip is disposed in the cavity of the handle, and an extended position, wherein the blunt tip protrudes out of a distal end of the tunneling tube, and the dissector is configured to create the subcutaneous pocket;
   an insertor comprising a cannula configured to move between a retracted position, wherein the cannula is disposed in the cavity of the handle, and an extended position, wherein the cannula is at least partially disposed in the passage of the tunneling tube; and
   an actuator disposed in the handle and operatively linked to the cannula, the dissector, and the insertor such that the actuator is configured to trigger the cannula, the blunt tip, and the insertor to move between their respective and extended positions;
   wherein the tunneling tube and the cannula are configured such that, when the tunneling tube and the cannula are at their respective extended positions, the cannula holds the device in the passage of the tunneling tube, and, when the tunneling tube is at or near the retracted position, the cannula moves toward its retracted position and releases the device out of the tunneling tube to deploy the device in the subcutaneous pocket.

2. The insertion tool of claim 1, wherein the dissector is configured to pivot from an operating position disposed along a first axis defined by the tunneling tube to an idle position disposed along a second axis, and the inserter is configured to pivot from an idle position disposed along a third axis to an operating position disposed along the first axis; and
   wherein the second axis extends at a first acute angle with respect to the first axis, and the third axis extends at a second acute angle with respect to the first axis.

3. The insertion tool of claim 2, wherein the handle comprises a hinge pivotably coupled to the dissector and the inserter.

4. The insertion tool of claim 3, wherein the inserter is configured to pivot between the operating and idle positions when the cannula is set in its retracted position, and the tunneling tube is configured to move between its retracted and extended positions when the inserter is set at the operating position.

5. The insertion tool of claim 1, wherein the actuator comprises a track extending along a portion of the handle and a slider knob configured to slide along the track and cause the tunneling tube, the blunt tip, and the cannula to move between their respective retracted and extended positions.

6. The insertion tool of claim 1, wherein the dissector comprises a first rod configured to move along the cavity of the handle and the passage of the tunneling tube, and the blunt tip is coupled to the first rod such that the first rod is configured to move the blunt tip along the cavity of the handle and the passage of the tunneling tube between the retracted and extended positions of the dissector.

7. The insertion tool of claim 1, wherein the insertor comprises a second rod configured to move along the cavity of the handle and the passage of the tunneling tube, and the cannula comprises a first end configured to hold and release the device and a second end coupled to the second rod such that the second rod is configured to move the cannula along the cavity of the handle and the passage of the tunneling tube between the retracted and extended positions of the insertor.

* * * * *